(12) United States Patent  
Sawaya (10) Patent No.: US 7,029,302 B2
(45) Date of Patent: Apr. 18, 2006

(54) CONNECTOR AND RADIATION TOMOGRAPHIC IMAGING APPARATUS

(75) Inventor: Takuji Sawaya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/967,412

(22) Filed: Oct. 18, 2004

(65) Prior Publication Data
US 2005/0090138 A1   Apr. 28, 2005

(30) Foreign Application Priority Data
Oct. 22, 2003 (JP) .............................. 2003-362097

(51) Int. Cl.
*H01R 13/15* (2006.01)
(52) U.S. Cl. .................... 439/260; 439/347; 439/327
(58) Field of Classification Search ................ 439/260, 439/347, 327, 370, 259, 263, 325, 267, 637, 439/635
See application file for complete search history.

(56) References Cited

U.S. PATENT DOCUMENTS

| | | | |
|---|---|---|---|
| 4,075,527 A | 2/1978 | Cummings | |
| 4,181,856 A | 1/1980 | Bone | |
| 4,560,221 A * | 12/1985 | Olsson | ........................ 439/373 |
| 4,712,178 A | 12/1987 | Tuy et al. | |
| 5,199,882 A | 4/1993 | Bates et al. | |
| 5,487,098 A | 1/1996 | Dobbs et al. | |
| 5,672,902 A | 9/1997 | Hatanaka et al. | |
| 5,757,878 A | 5/1998 | Dobbs et al. | |
| 5,795,162 A | 8/1998 | Lambert | |
| 5,846,094 A | 12/1998 | Murray et al. | |
| 6,139,337 A | 10/2000 | Englert et al. | |
| 6,688,902 B1 * | 2/2004 | Yoon et al. | .................. 439/260 |
| 2002/0085665 A1 | 7/2002 | Hoffman et al. | |

FOREIGN PATENT DOCUMENTS

JP   2003-033344   2/2003

OTHER PUBLICATIONS

European Search Report, Great Britain; European Patent Application No. 04256455.9-2305, 2 pgs.
"Flexible Cable Connection for Detector Module", NonProvisional Application as Filed, U.S. Appl. No. 09/705,590, Filed Nov. 3, 2000, 12 pgs.

* cited by examiner

*Primary Examiner*—Ross Gushi
(74) *Attorney, Agent, or Firm*—Carl B. Horton, Esq.; Armstrong Teasdale LLP (57) ABSTRACT

A connector includes a clamp member inserted through a second insert opening into a socket portion such that the surfaces of the clamp member come into contact with the surface of a retaining member and the side wall of the socket portion running along a surface of the retaining member to press the retaining member, and such that a plurality of boards received in the socket portion are fixed to connect a plurality of first electrodes with a plurality of second electrodes.

15 Claims, 10 Drawing Sheets

CONNECTOR AND RADIATION TOMOGRAPHIC IMAGING APPARATUS

CROSS REFERENCE TO RELATED APPLICATION

This application claims the benefit of Japanese Application No. 2003-362097 filed Oct. 22, 2003.

BACKGROUND OF THE INVENTION

The present invention relates to a connector and a radiation tomographic imaging apparatus, and particularly to a connector applied to detecting means in which a plurality of detector elements for detecting radiation and outputting projection data are disposed, and a radiation tomographic imaging apparatus employing such a connector.

Known radiation tomographic imaging apparatuses include an X-ray CT (computed tomography) apparatus that employs X-ray radiation to produce an image representing a cross-sectional plane of a subject to be imaged. The X-ray CT apparatus is used in a wide variety of applications including medical and industrial applications with a human body or an inanimate object as a subject to be imaged.

The X-ray CT apparatus scans the subject to be imaged around the body axis of the subject to be imaged, and employs an X-ray tube to irradiate the subject to be imaged with X-rays in a plurality of view directions, for example. An X-ray detector in which detector elements for detecting X-rays are disposed detects X-rays passing through the subject to be imaged in the plurality of view directions for each view direction, and outputs projection data from electrodes connected to the X-ray detector. Then, a data collecting section having a board on which a driving circuit is formed to collect projection data collects the projection data output by the electrodes connected to the X-ray detector from electrodes on the board. Based on the collected projection data, a tomographic image of an imaged region in the subject to be imaged is reconstructed and produced.

The imaged regions in the subject to be imaged and the purposes of imaging with the X-ray CT apparatus are becoming increasingly diverse in recent years, and accordingly, the X-ray CT apparatus is required to have improved image quality including resolution, and increased imaging speed. To respond to such requirements, the X-ray CT apparatus has an X-ray detector in which a plurality of detector elements are arranged in the form of an array to obtain a plurality of tomographic images during one scan rotation around the subject to be imaged, and the number of arranged detector elements is on the increase. (For example, see Patent Document 1).

[Patent Document 1] Japanese Patent Application Laid Open No. 2003-33344.

Such an X-ray detector has a plurality of X-ray detector modules in each of which a plurality of detector elements for detecting X-rays are arranged in the form of an array, and to facilitate manufacture, the plurality of X-ray detector modules are arranged side by side in both the channel direction and body axis direction. Moreover, in the X-ray detector, the plurality of detector elements are arranged at high density to improve resolution, and the electrodes for outputting projection data from the detector elements to the data collecting section are also disposed at high density because they are formed in a limited region.

Similarly, in the data collecting section for collecting projection data output from the X-ray detector, a plurality of boards on which driving circuits for collecting the projection data are mounted are disposed corresponding to the plurality of X-ray detector modules making up the X-ray detector, and the electrodes to which the projection data is input are formed on the each board at high density corresponding to the density increase of the electrodes for outputting the projection data from the X-ray detector elements.

When the electrodes in the X-ray detector and those on the boards in the data collecting section are connected to one another, the conventional method has been to use thermal compression bonding or connectors, for example.

With the conventional thermal compression bonding, however, the increased compactness of the electrodes reduces the space available for the connection work, and it becomes difficult to connect the electrodes to one another at high precision. With the conventional connectors, the high compactness of the electrodes makes it difficult to connect between the electrodes and to fix the boards on which the electrodes are formed to the connector with sufficient rigidity.

Moreover, when maintenance is carried out on an X-ray detector array constituted of a plurality of X-ray detector modules, it suffices to replace only the one malfunctioning X-ray detector module in the small space where the plurality of boards are disposed; but with the conventional connection by thermal compression bonding, the modules cannot be made removable, and with the conventional connectors, the space for insertion/removal work is small because the plurality of boards are present, and the insertion/removal work is difficult to do.

As described above, in the conventional X-ray CT apparatus, one example of a radiation tomographic imaging apparatus, as the number of detector elements in the X-ray detector is increased in line with the need for improved image quality and imaging speed, the electrodes are arranged at higher density, and it becomes difficult to fix the boards to the connector with sufficient rigidity and to insert/remove the board into/from the connector because of the small space available for disposing the boards, which makes it difficult to do maintenance work.

SUMMARY OF THE INVENTION

It is therefore an object of the present invention to provide a connector and a radiation tomographic imaging apparatus by which a board can be easily fixed with sufficient rigidity and the board can be easily inserted/removed, thereby facilitating maintenance work.

To attain the aforementioned objects, a connector in accordance with the present invention comprises: a connector body provided with a first insert opening for inserting therethrough a board, and a socket portion for receiving at least part of said board inserted through said first insert opening; a retaining member disposed in said socket portion with its one surface facing a surface of said board so that said retaining member is pressed to fix said board received in said socket portion; and a clamp member for pressing said retaining member by coming into contact with a side wall of said socket portion running along a surface of said retaining member and the other surface of said retaining member, wherein said connector body is provided with a second insert opening for inserting therethrough said clamp member, said second insert opening communicating with said socket portion, said retaining member is formed to have a smaller thickness at one end near said second insert opening than that at the other end, and said clamp member is formed to have a larger thickness at one end near said second insert opening than that at the other end, and is inserted through said second insert opening into said socket portion to press said retaining member.

According to the present invention, by inserting the clamp member through the second insert opening into the socket portion, the surface of the clamp member comes into contact with the surface of the retaining member and the side wall of the socket portion running along a surface of the retaining member to press the retaining member in the socket portion, whereby the board received in the socket portion is fixed. Since the retaining member is formed to have a smaller thickness at one end near the second insert opening than that at the other end, and the clamp member is formed to have a larger thickness at one end near the second insert opening than that at the other end, the other end of the socket portion on the opposite side of the second insert opening can be easily pressed, whereby the board is fixed with uniform rigidity.

To attain the aforementioned objects, a radiation tomographic imaging apparatus in accordance with the present invention comprises: detecting means in which detector elements are disposed for detecting radiation emitted to an imaged region in a subject to be imaged and passing through said imaged region, and for outputting projection data; collecting means comprising a board provided on at least one surface with first electrodes to which said projection data from said detector elements is input, and formed with a driving circuit for collecting said input projection data; and a connector provided with, corresponding to said first electrodes, second electrodes for outputting the projection data from said detector elements to said first electrodes, for connecting said first electrodes with said second electrodes, said connector comprising: a connector body provided with a first insert opening for inserting therethrough said board, and a socket portion for receiving said first electrodes on said board inserted through said first insert opening; a retaining member provided on one surface with said second electrodes facing said first electrodes when said board is inserted, and disposed in said socket portion so that said retaining member is pressed to connect said first electrodes with said second electrodes and fix said board received in said socket portion; and a clamp member for pressing said retaining member by coming into contact with a side wall of said socket portion running along a surface of said retaining member and the other surface of said retaining member, wherein said connector body is provided with a second insert opening for inserting therethrough said clamp member, said second insert opening communicating with said socket portion, said retaining member is formed to have a smaller thickness at one end near said second insert opening than that at the other end, and said clamp member is formed to have a larger thickness at one end near said second insert opening than that at the other end, and is inserted through said second insert opening into said socket portion to press said retaining member.

According to the present invention, by inserting the clamp member through the second insert opening into the socket portion, the surface of the clamp member comes into contact with the other surface of the retaining member and the side wall of the socket portion running along a surface of the retaining member to press the retaining member in the socket portion, whereby the board received in the socket portion is fixed to connect the first and second electrodes. Since the retaining member is formed to have a smaller thickness at one end near the second insert opening than that at the other end, and the clamp member is formed to have a larger thickness at one end near the second insert opening than that at the other end, the socket portion can be easily pressed at the other end on the opposite side of the second insert opening, whereby the board is fixed with uniform rigidity to connect the first and second electrodes.

Therefore, the present invention provides a connector and a radiation tomographic imaging apparatus by which a board can be easily fixed with sufficient rigidity and the board can be easily inserted/removed, thereby facilitating maintenance work.

Further objects and advantages of the present invention will be apparent from the following description of the preferred embodiments of the invention as illustrated in the accompanying drawings.

DETAILED DESCRIPTION OF THE INVENTION

Exemplary embodiments in accordance with the present invention will now be described in detail with reference to the accompanying drawings.

Figure 1:
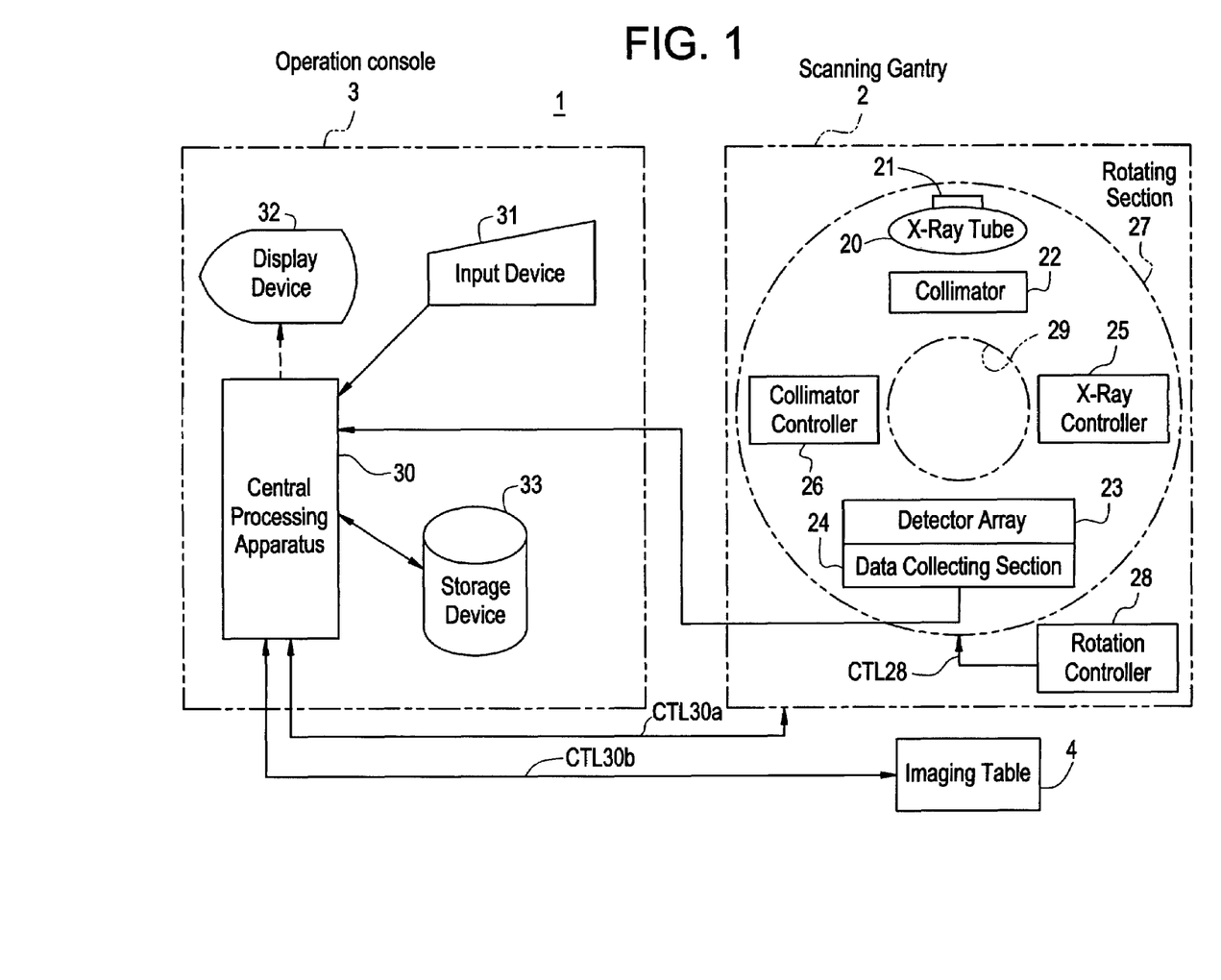
FIG. 1 is a block diagram showing the overall configuration of an X-ray CT apparatus that is an embodiment of a radiation tomographic imaging apparatus in accordance with the present invention
Figure 2:
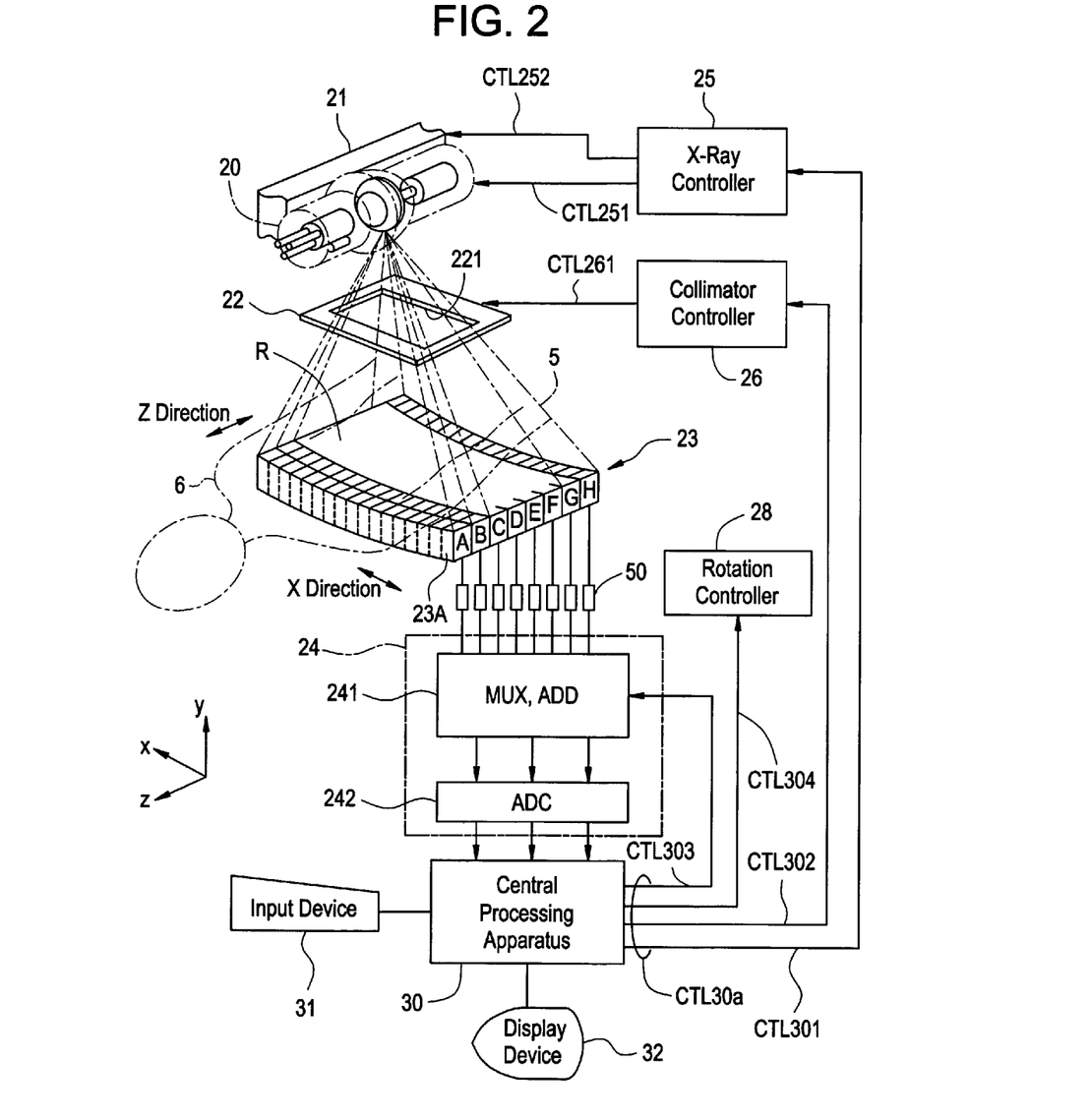
FIG. 2 is a configuration diagram showing a main portion in the X-ray CT apparatus that is an embodiment of the radiation tomographic imaging apparatus in accordance with the present invention.

First, the configuration of a radiation tomographic imaging apparatus of an embodiment in accordance with the present invention will be described. FIG. 1 is a block diagram showing the overall configuration of an X-ray CT apparatus 1 that is an embodiment of the radiation tomographic imaging apparatus in accordance with the present invention, and FIG. 2 is a configuration diagram showing a main portion in the X-ray CT apparatus 1 that is an embodiment of the radiation tomographic imaging apparatus in accordance with the present invention.

As shown in FIG. 1, the X-ray CT apparatus 1 of the present embodiment comprises a scan gantry 2, an operation console 3, and an imaging table 4.

The scan gantry 2 comprises an X-ray tube 20, an X-ray tube moving section 21, a collimator 22, an X-ray detector array 23, a data collecting section 24, an X-ray controller 25, a collimator controller 26, a rotating section 27 and a rotation controller 28 as main components. The X-ray tube 20 and X-ray detector array 23 are disposed to face each other across an X-ray irradiated space 29.

The X-ray detector array 23 in the scan gantry 2 corresponds to the detecting means in accordance with the present invention, and the data collecting section 24 in the scan gantry 2 corresponds to the collecting means in accordance with the present invention.

The X-ray tube 20 emits X-rays 5 at certain intensity through the collimator 22 to an imaged region R in a subject to be imaged 6 based on a control signal CTL251 from the X-ray controller 25.

The X-ray tube moving section 21 moves the emission center of the X-ray tube 20 in the body axis direction of the subject to be imaged 6 placed on the imaging table 4 within the X-ray irradiated space 29 in the scan gantry 2 (i.e., in the direction orthogonal to the drawing plane of FIG. 1, and in the z-direction of FIG. 2), based on a control signal CTL252 from the X-ray controller 25.

The collimator 22 is disposed between the X-ray tube 20 and X-ray detector array 23, and adjusts the emission extent of the X-rays 5 emitted from the X-ray tube 20 by adjusting the degree of openness of an aperture based on a control signal CTL261 from the collimator controller 26 to block the X-rays in the channel direction x and body axis direction z and form the X-rays 5 into a cone shape having predetermined widths in the channel direction x and body axis direction z. The adjustment of the degree of openness of the aperture in the collimator 22 is achieved by independently moving two plates provided in the channel direction x and those provided in the body axis direction z, for example.

The X-ray detector array 23 comprises eight X-ray detector modules 23A, 23B, 23C, 23D, 23E, 23F, 23G and 23H, and the eight X-ray detector modules 23A, 23B, 23C, 23D, 23E, 23F, 23G and 23H are arranged side-by-side in the sequence of row A to row H in the body axis direction z.

Figure 3:
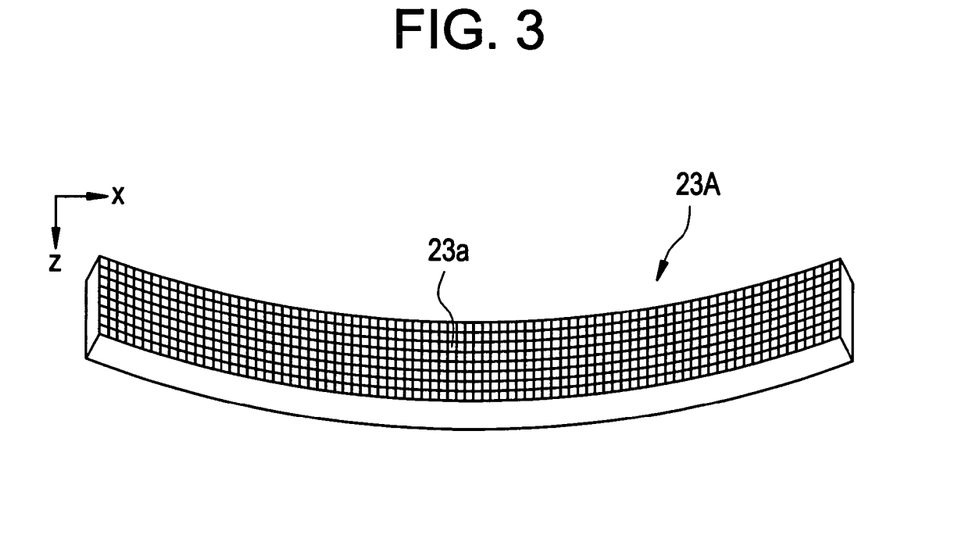
FIG. 3 is a configuration diagram showing an X-ray detector module in the X-ray CT apparatus that is an embodiment of the radiation tomographic imaging apparatus in accordance with the present invention.

FIG. 3 is a configuration diagram showing an X-ray detector module 23A of a row A among the eight X-ray detector modules 23A, 23B, 23C, 23D, 23E, 23F, 23G and 23H making up the X-ray detector array 23. As shown in FIG. 3, the X-ray detector module 23A has detector elements 23a for detecting X-rays arranged in an array in the channel direction x and body axis direction z. The plurality of detector elements 23a arranged in a two-dimensional manner form as a whole a cylindrically concaved X-ray impingement surface. In the channel direction x, 1000 detector elements 23a, for example, are arranged, and in the body axis direction z, eight detector elements 23a, for example, are arranged. The X-ray detector modules 23B, 23C, 23D, 23E, 23F, 23G and 23H from row B to row H are similar to the X-ray detector module 23A of the row A shown in FIG. 3.

The detector elements 23a are each made of a solid state detector having a scintillator (not shown) for converting detected X-rays into light and a photodiode (not shown) for converting the light converted by the scintillator into an electrical charge, for example. It should be noted that the detector elements 23a are not limited thereto but may be semiconductor X-ray detector elements using cadmium telluride (CdTe) or the like, or ionization chamber X-ray detector elements using xenon (Xe) gas, for example.

Figure 4A:
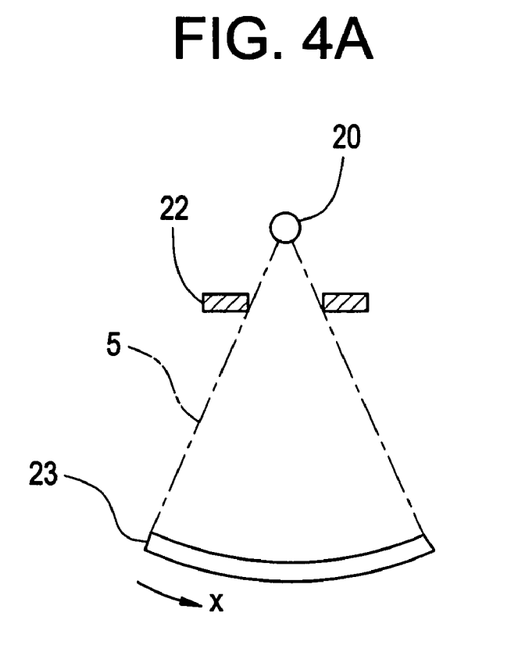
FIG. 4 is a diagram showing the mutual relationship among an X-ray tube, a collimator and an X-ray detector array in the X-ray CT apparatus as a radiation tomographic imaging apparatus in accordance with the embodiment of the present invention, in which (a) is a view in the body axis direction, and (b) is a view in the channel direction.
Figure 4B:
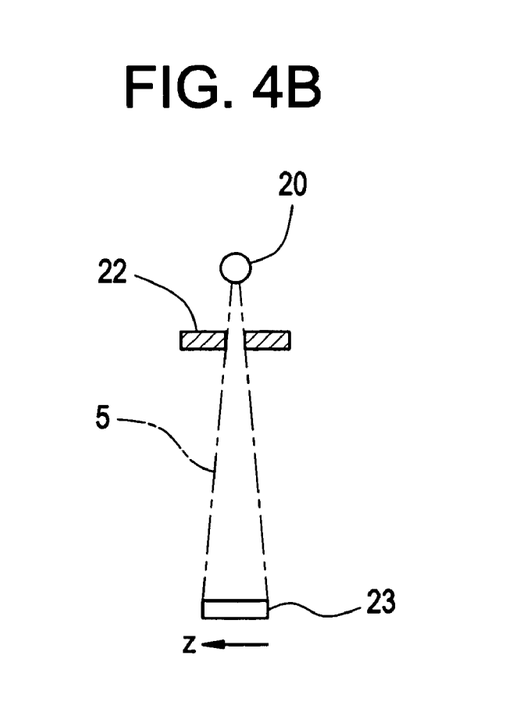
Figure 5:
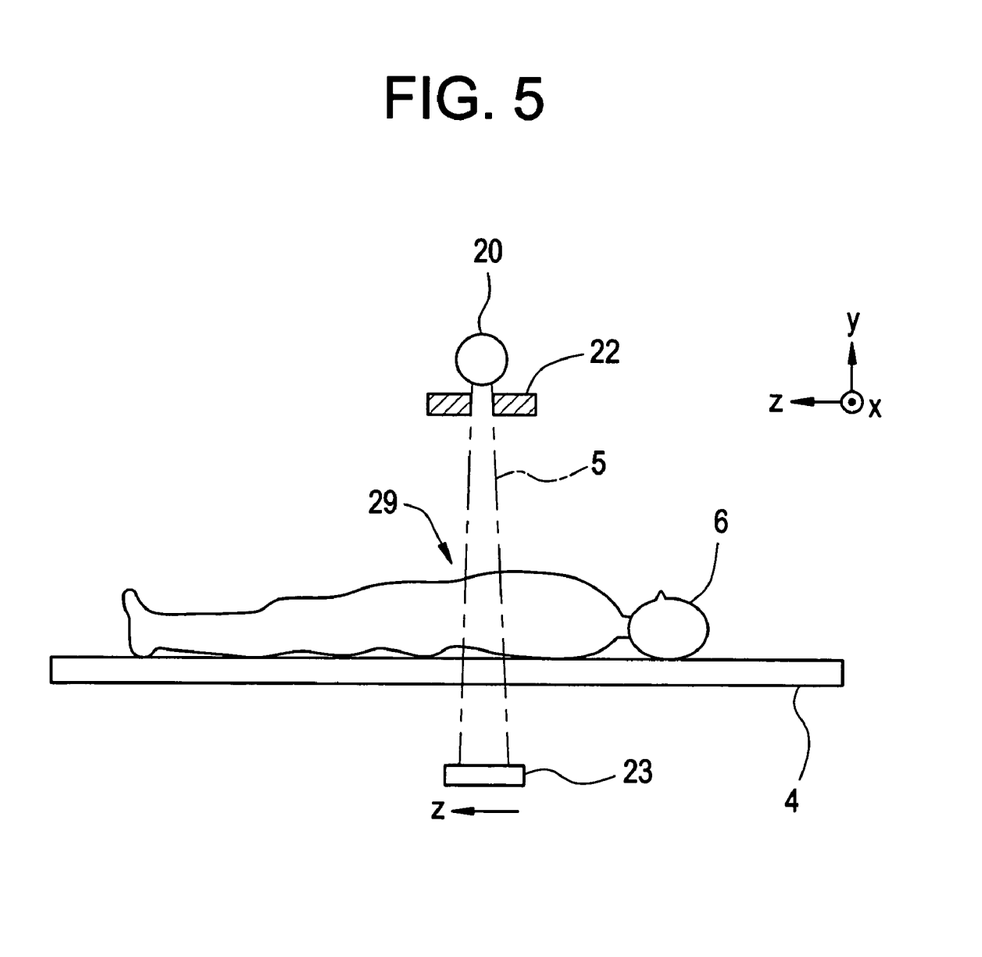
FIG. 5 is a diagram showing the mutual relationship among the X-ray tube, collimator and X-ray detector array in the X-ray CT apparatus that is an embodiment of a radiation tomographic imaging apparatus in accordance with the present invention, in which imaging of a subject to be imaged is shown as viewed in the channel direction.

FIGS. 4 and 5 are diagrams showing the mutual relationship among the X-ray tube 20, collimator 22 and X-ray detector array 23. In FIG. 4, (a) is a view in the body axis direction z, and (b) is a view in the channel direction x. FIG. 5 is a diagram showing imaging of the subject to be imaged 6 as viewed in the channel direction x, as in FIG. 4(b).

As shown in FIGS. 4(a) and (b), X-rays 5 emitted from the X-ray tube 20 are formed into cone-shaped X-rays 5 having a certain cone angle by the collimator 22, and are caused to impinge upon the detector elements 23a in a predefined area in the X-ray detector array 23. As shown in FIG. 5, when the subject to be imaged 6 is imaged, the subject to be imaged 6 placed on the imaging table 4 is carried into the X-ray irradiated space 29 and is scanned around the body axis thereof, and the X-rays 5 are emitted from the X-ray tube 20 toward the imaged region R in the subject to be imaged 6. The X-rays 5 emitted from the X-ray tube 20 pass through the collimator 22 and then the subject to be imaged 6, and are detected by the X-ray detector array 23. The X-ray detector array 23 then outputs projection data based on the detected X-rays passing through the subject to be imaged 6.

The data collecting section 24 collects the projection data from the individual detector elements 23a in the X-ray detector array 23 and outputs them to the operation console 3. As shown in FIG. 2, the data collecting section 24 has driving circuits including a selection/addition switching circuit (MUX, ADD) 241 and an analog-to-digital converter circuit (ADC) 242. The driving circuits including the selection/addition switching circuit (MUX, ADD) 241 and analog-to-digital converter circuit (ADC) 242 are formed on boards, and connected to the X-ray detector array 23 via connectors 50. Each connector 50 is provided in association with one of the X-ray detector modules 23A, 23B, 23C, 23D, 23E, 23F, 23G and 23H in the X-ray detector array 23, for example, and the boards are disposed close to each other in a small space, as described earlier. The connectors 50 will be further described later.

The selection/addition switching circuit 241 selects or adds in a varying combination the projection data from the detector elements 23a in the X-ray detector array 23 in response to a control signal CTL303 from the central processing apparatus 30 in the operation console 3 to collect the projection data, and outputs the collected projection data to the analog-to-digital converter circuit 242. The analog-to-digital converter circuit 242 converts the projection data that are selected or added in an arbitrary combination at the selection/addition switching circuit 241 from analog signals to digital ones, and outputs them to the central processing apparatus 30 in the operation console 3.

The X-ray controller 25 outputs the control signal CTL251 to the X-ray tube 20 in response to a control signal CTL301 from the central processing apparatus 30 in the operation console 3 for controlling X-ray emission. The X-ray controller 25 also outputs the control signal CTL252 to the X-ray tube moving section 21 in response to the control signal CTL301 from the central processing apparatus 30 in the operation console 3 for moving the emission center of the X-ray tube 20 by a commanded distance in the body axis direction z.

The collimator controller 26 outputs the control signal CTL261 to the collimator 22 in response to a control signal CTL302 from the central processing apparatus 30 in the operation console 3 for controlling the degree of openness of the aperture 221 in the collimator 22 to shape the X-rays 5 emitted from the X-ray tube 20, and cause the X-rays 5 to impinge upon a desired area in the X-ray detector array 23.

The rotating section 27 is rotated in a predetermined direction based on a control signal CTL28 from the rotation controller 28. The rotating section 27 supports the X-ray tube 20, X-ray tube moving section 21, collimator 22, X-ray detector array 23, data collecting section 24, X-ray controller 25 and collimator controller 26, and the positional relationship of these components relative to the subject to be imaged 6 carried into the X-ray irradiated space 29 varies with the rotation of the rotating section 27. By rotating the rotating section 27, the X-rays 5 are emitted from a plurality of view directions around the body axis of the subject to be imaged 6, and the X-rays 5 passing through the subject to be imaged 6 are detected.

The rotation controller 28 outputs the control signal CTL28 to the rotating section 27 in response to a control signal CTL304 from the central processing apparatus 30 in the operation console 3 for rotating the rotating section 27 a desired number of times in a predetermined direction.

The operation console 3 comprises the central processing apparatus 30, an input device 31, a display device 32 and a storage device 33 as main components.

The central processing apparatus 30 is comprised of, for example, a microcomputer, and has programs corresponding to several kinds of functions. The central processing apparatus 30 outputs a control signal CTL30b to the imaging table 4 in response to a command input from the input device 31 for carrying the imaging table 4 on which the subject to be imaged 6 is placed into/out of the X-ray irradiated space 29 of the scan gantry 2.

The central processing apparatus 30 outputs the control signal CTL304 to the rotation controller 28 in the scan gantry 2 in response to a command to start a multi-slice scan input from the input device 31, and causes the rotating section 27 in the scan gantry 2 to rotate a commanded number of times in a predetermined direction.

The central processing apparatus 30 also outputs the control signal CTL301 to the X-ray controller 25 to cause the X-ray tube 20 in the scan gantry 2 to emit the X-rays 5.

The central processing apparatus 30 then outputs the control signal CTL301 to the X-ray controller 25 in response to information on the imaged region R in the subject to be imaged 6 input from the input device 31, and causes the emission center of the X-ray tube 20 to move in the body axis direction z by a commanded distance. At that time, the central processing apparatus 30 also outputs the control signal CTL302 to the collimator controller 26 for controlling the collimator 22 to have a predetermined degree of aperture openness so as to emit the X-rays 5 over a predefined region.

Moreover, the central processing apparatus 30 outputs the control signal CTL303 to the selection/addition switching circuit 241 in the data collecting section 24 in response to the information on the imaged region R in the subject to be imaged 6 input from the input device 31 so that the projection data obtained at the detector elements 23a in the X-ray detector array 23 are selected or added in a varying combination. The central processing apparatus 30 also performs pre-processing such as offset correction on the projection data collected by the data collecting section 24.

The central processing apparatus 30 then performs image reconstruction based on the projection data in the plurality of view directions to generate image data for a plurality of tomographic images. For the image reconstruction, a filtered backprojection technique is employed, for example. The image data thus generated are output to and displayed on the display device 32.

The input device 31 is provided for inputting information such as imaging conditions to the central processing apparatus 30, and is comprised of a keyboard and mouse, for example. The input device 31 may be connected to the scan gantry 2 or imaging table 4.

The display device 32 displays the tomographic image that is reconstructed and produced or other several kinds of information in response to a command from the central processing apparatus 30.

The storage device 33 stores several kinds of data, reconstructed images, programs etc., and the stored data are accessed by the central processing apparatus 30 as needed.

The connector 50 of the present embodiment in accordance with the present invention will now be described.

Figure 6:
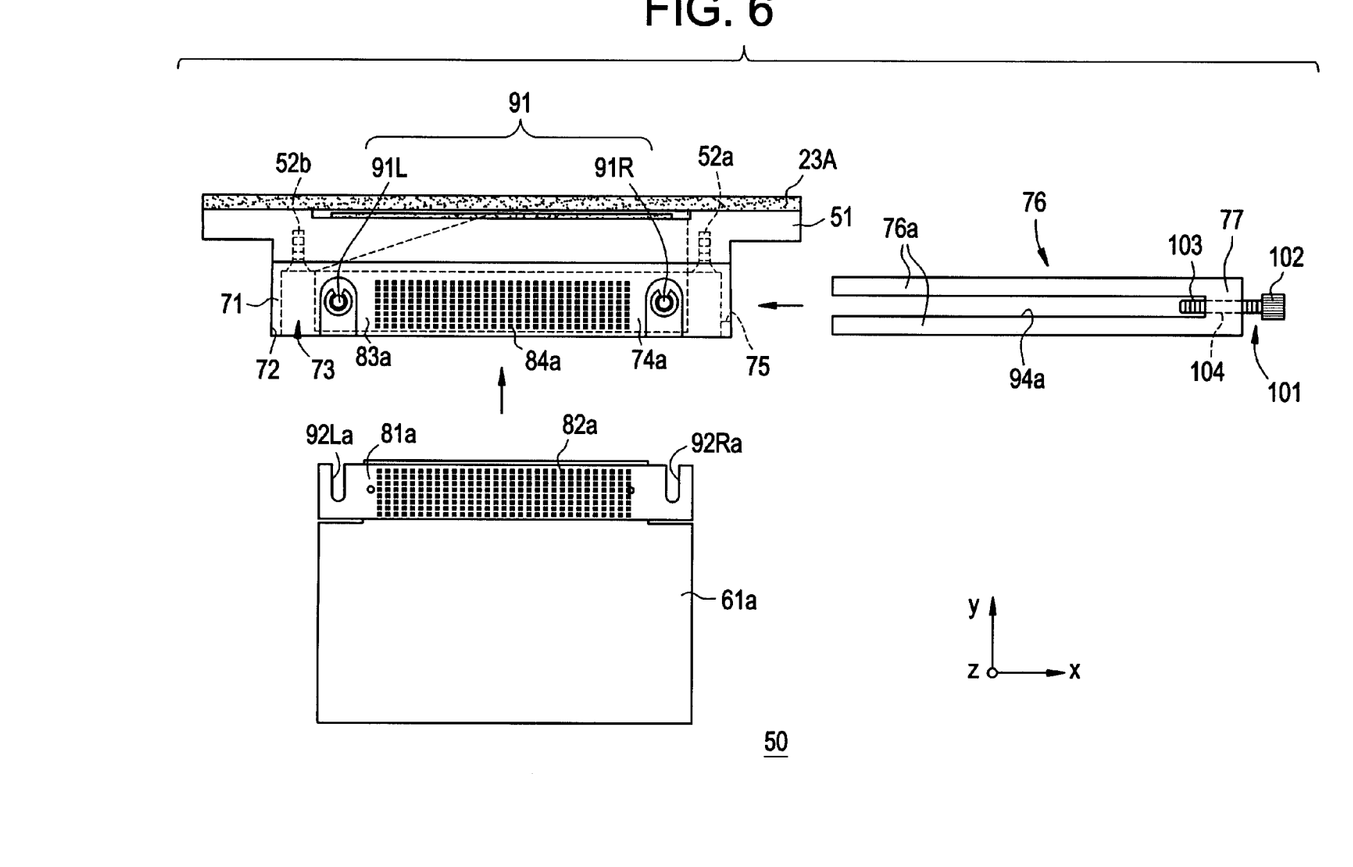
FIG. 6 is a configuration diagram showing the configuration of a connector of an embodiment in accordance with the present invention, as viewed in one side of the body axis direction.
Figure 7:
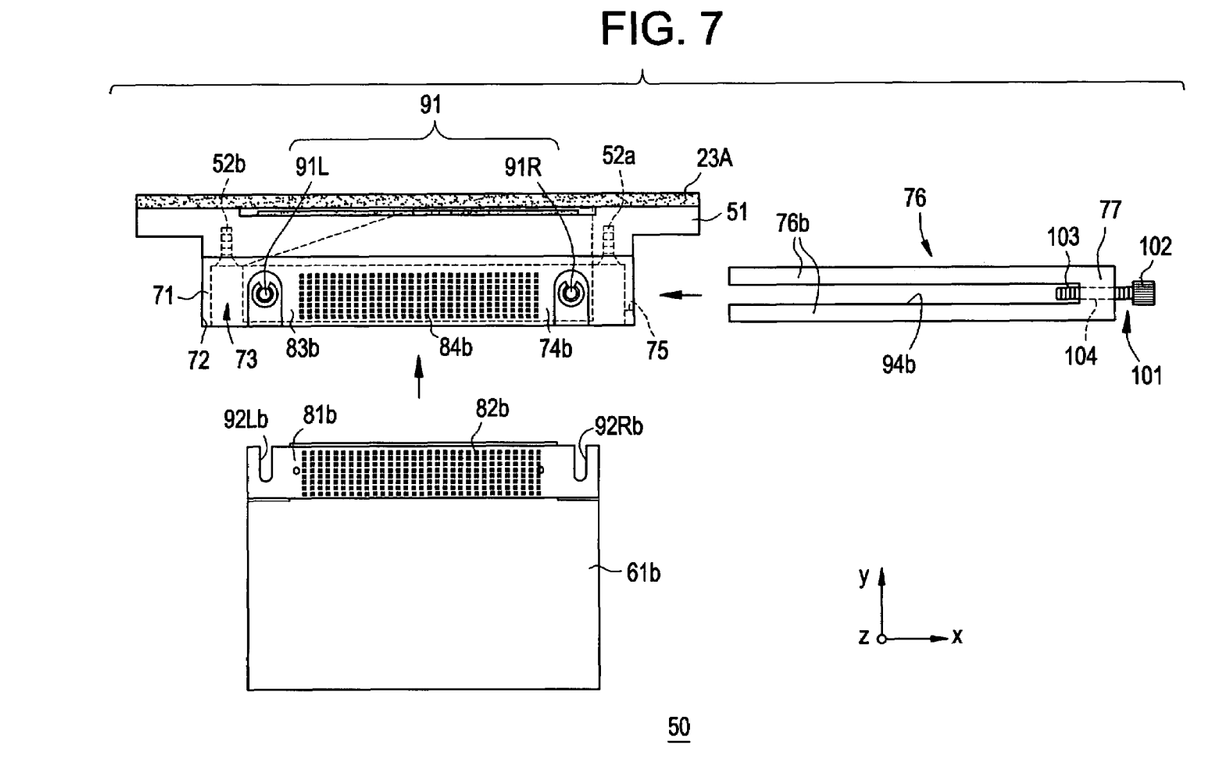
FIG. 7 is a configuration diagram showing the configuration of the connector of the embodiment in accordance with the present invention, as viewed in the other side with respect to FIG. 6.
Figure 8:
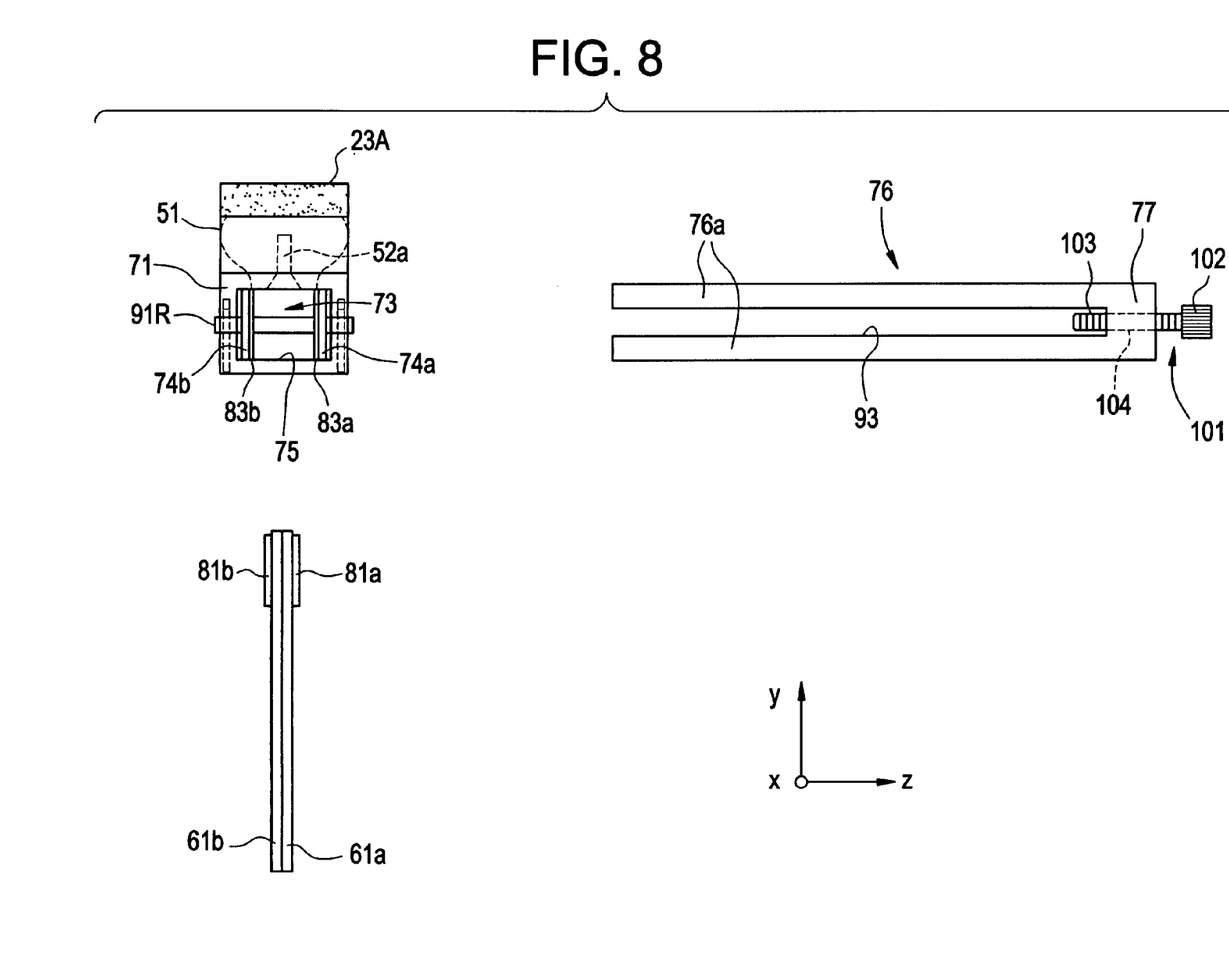
FIG. 8 is a configuration diagram showing the configuration of the connector of the embodiment in accordance with the present invention, as viewed in the channel direction x.
Figure 9:
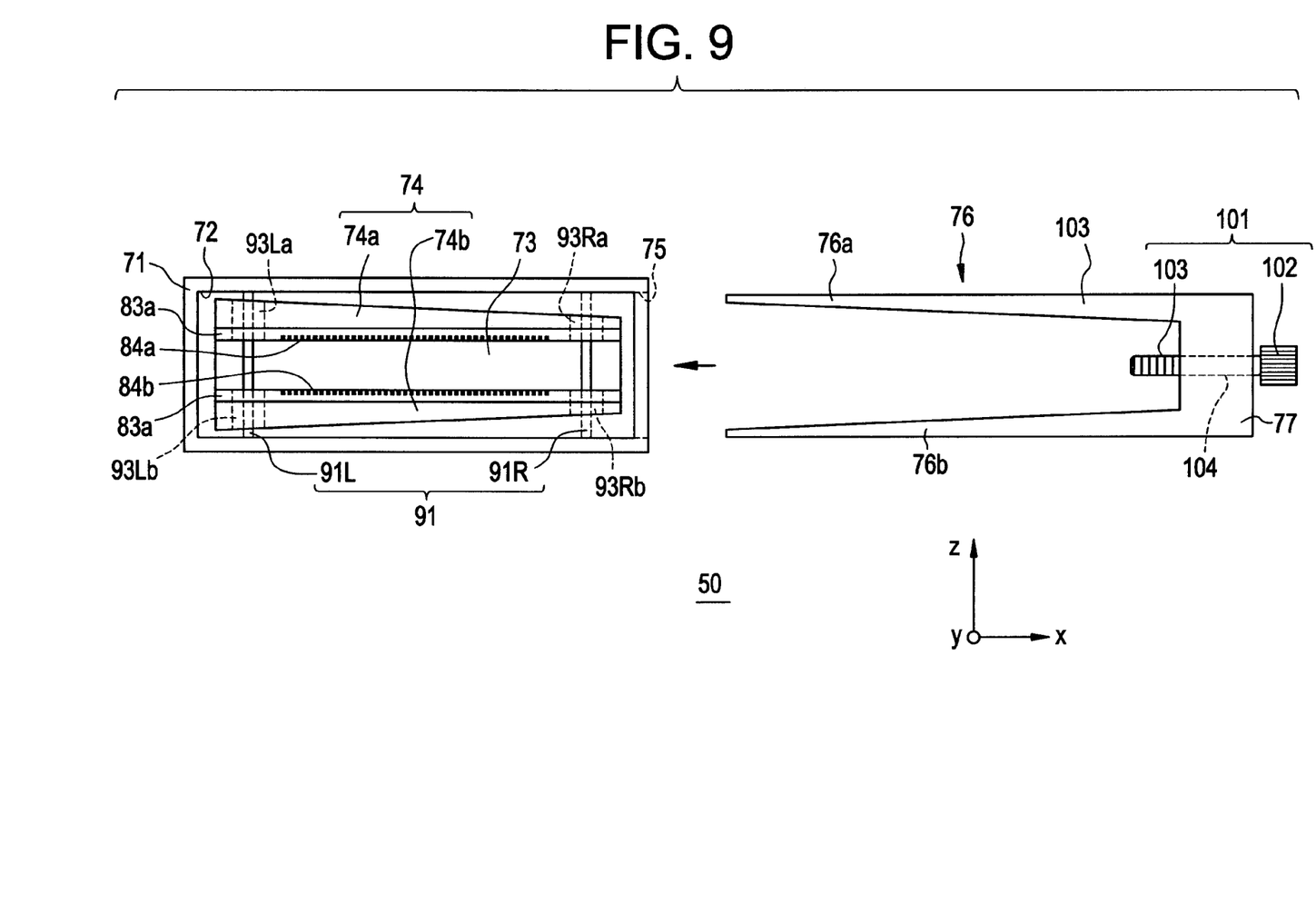
FIG. 9 is a configuration diagram showing the configuration of the connector of the embodiment in accordance with the present invention, as viewed in the X-ray emission direction y.
Figure 10A:
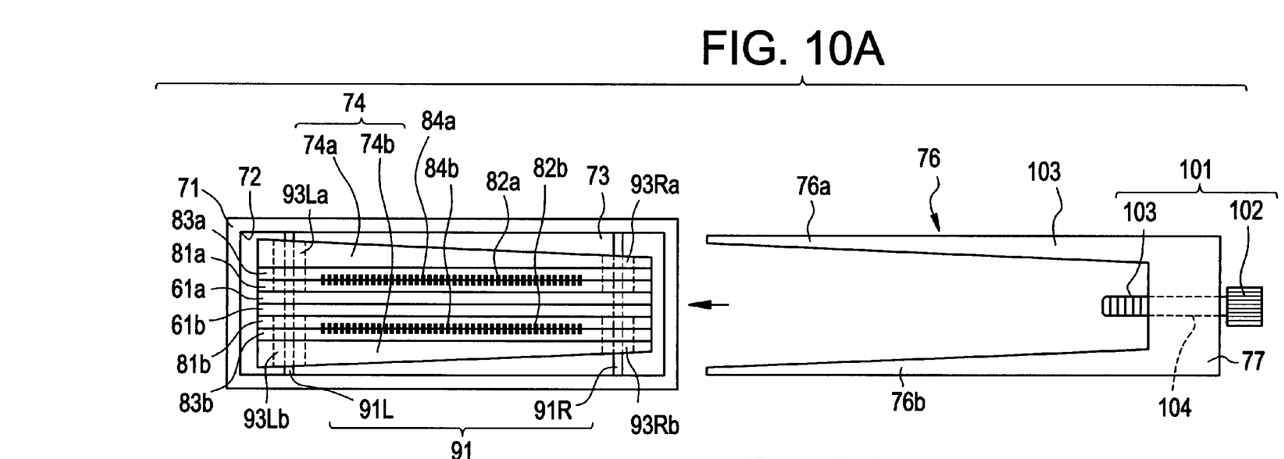
FIG. 10 is a configuration diagram showing the configuration of the connector of the embodiment in accordance with the present invention, as viewed in the X-ray emission direction y; in which (a) shows a condition after inserting first and second boards through a first insert opening into a socket portion, and (b) shows a condition after inserting a clamp member through a second insert opening to connect first electrodes on the first and second boards with second electrodes of the connector.
Figure 10B:
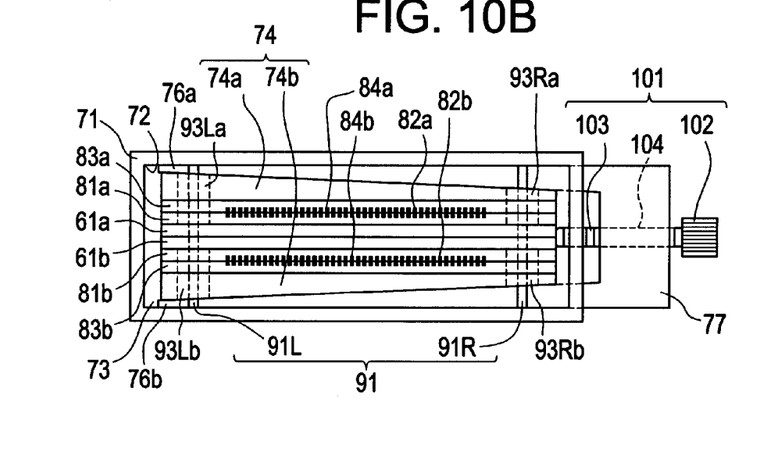

FIGS. 6, 7, 8, 9 and 10 are configuration diagrams showing the configuration of the connector 50 of the present embodiment in accordance with the present invention, in which the connector 50 provided for one X-ray detector module 23A belonging to the X-ray detector array 23 in the X-ray CT apparatus 1 in FIG. 2 is illustrated. FIG. 6 is a view from one side of the body axis direction z in FIG. 2, and FIG. 7 is a view from the other side with respect to that of FIG. 6. FIG. 8 is a view from the channel direction x, and FIGS. 9 and 10 are views from the X-ray emission direction y. FIGS. 6, 7, 8 and 9 show a condition before connecting first electrodes 82a and 82b on first and second boards 61a and 61b with second electrodes 84a and 84b in the connector 50, FIG. 10(a) shows a condition after inserting the first and second boards 61a and 61b through first insert opening 72 into a socket portion 73, and FIG. 10(b) shows a condition after inserting a clamp member 76 through a second insert opening 75 to connect the first electrodes 82a and 82b on the first and second boards 61a and 61b with the second electrodes 84a and 84b in the connector 50.

As shown in FIGS. 6–10, the connector 50 of the present embodiment comprises a connector body 71, a retaining member 74 and a clamp member 76.

The connector 50 of the present embodiment is provided for connecting the first and second boards 61a and 61b belonging to the aforementioned data collecting section 24 with the X-ray detector module 23A belonging to the X-ray detector array 23.

The first and second boards 61a and 61b have the aforementioned driving circuits, and are provided with first electrode plates 81a and 81b, respectively, as shown in FIGS. 6 and 7. The first electrode plates 81a and 81b are made of dielectric plates, and they are provided with the first electrodes 82a and 82b to which projection data from the detector elements 23a are input, in the form of a matrix on one surface each, corresponding to the plurality of detector elements 23a in the X-ray detector module 23A. The first electrodes 82a and 82b are made using a spring pin, for example, that is pressed against a predefined position by a spring and is movable in a pressing direction of the spring, and they are provided for inputting projection data from the detector elements 23a to the first and second boards 61a and 61b. Moreover, the first electrode plates 81a and 81b are provided at their ends with board guide cuts 92R and 92L corresponding to a guide member 91, which will be discussed later.

The connector 50 of the present embodiment connects the two sets of first electrodes 82a and 82b with the two sets of second electrodes 84a and 84b in the connector 50, with the first and second boards 61a and 61b having the first electrodes 82a and 82b on one surface each having the other surfaces thereof abutted against each other.

The connector body 71 is made of, for example, a formed metal such as aluminum, and is securely joined to a joint member 51 provided in the X-ray detector module 23A via joint screws 52a and 52b, as shown in FIGS. 6–8. The connector body 71 comprises a first insert opening 72, a socket portion 73, a second insert opening 75, and a guide member 91.

The first insert opening 72 is formed in a rectangular shape to allow the first and second boards 61a and 61b to be inserted.

The socket portion 73 is formed in a rectangular parallelepiped shape in the interior of the connector body 71 to receive a region in which the first electrodes 82a and 82b are formed on the first and second boards 61a and 61b inserted through the first insert opening 72.

The second insert opening 75 is formed in a rectangular shape to allow the clamp member 76 to be inserted, and it communicates with the socket portion 73.

The guide member 91 is provided in the connector body 71 for guiding the boards 61a and 61b inserted through the first insert opening 72 in position. In the present embodiment, first and second guide rods 91R and 91L serving as the guide member 91 are fixed at their ends to the side wall of the socket portion 73 running along a surface of the inserted boards 61a and 61b. The first guide rod 91R is provided at one end of the socket portion 73 near the second insert opening 75, and the second guide rod 91L is provided at the other end of the socket portion 73 on the opposite side of the second insert opening 75. By inserting the board guide cuts 92R and 92L in the first and second boards 61a and 61b to fit over the first and second guide rods 91R and 91L, the first electrodes 82a and 82b on the first and second boards 61a and 61b are received in the socket portion 73 in position. The guide member 91 is not limited to the first and second guide rods 91R and 91L of the present embodiment, and may be a pair of guide plates, for example, comprising a medial slit corresponding to the thickness of the boards 61a and 61b to be inserted. While two guide rods, i.e., the first and second guide rods 91R and 91L, are provided in the present embodiment, one guide rod may be provided.

The retaining member 74 is comprised of first and second retaining plates 74a and 74b. The first and second retaining plates 74a and 74b are disposed in the socket portion 73 so that when the boards 61a and 61b are inserted through the first insert opening 72, the surfaces of the boards 61a and 61b on which the first electrodes 82a and 82b are disposed face the surfaces on which the second electrodes 84a and 84b are provided.

As shown in FIGS. 9 and 10, the first and second retaining plates 74a and 74b comprise first through holes 93Ra and 93Rb and second through holes 93La and 93Lb through which the first and second guide rods 91R and 91L in the socket portion 73 run, respectively. The first guide rod 91R runs through the first through holes 93Ra and 93Rb, and the second guide rod 91L runs through the second through holes 93La and 93Lb. The first through holes 93Ra and 93Rb have a larger diameter than the outer diameter of the first guide rod 91R, and the second through holes 93La and 93Lb have a larger diameter than the outer diameter of the second guide rod 91L. Thus, the first and second retaining plates 74a and 74b are movable in the socket portion 73 in a direction of axes of the first guide rod 91R running through the first through holes 93Ra and 93Rb and of the second guide rod 91L running through the second through holes 93La and 93Lb.

The first and second retaining plates 74a and 74b are made of a formed resin, for example, and are provided with second electrode plates 83a and 83b on one surface each. The second electrode plates 83a and 83b are made of a flexible dielectric plate, and have the second electrodes 84a and 84b on one surface each. The second electrodes 84a and 84b are made in the form of a planar matrix on one surface of each of the second electrode plates 83a and 83b corresponding to the first electrodes 82a and 82b, for outputting projection data from the detector elements 23a to the first electrodes 82a and 82b on the first and second boards 61a and 61b. The first electrodes 82a and 82b and second electrodes 84a and 84b are connected by bringing tips of the pins of the first electrodes 82a and 82b into contact with the surfaces of the second electrodes 84a and 84b.

The first and second retaining plates 74a and 74b have a larger area than a region in the second electrode plates 83a and 83b in which the second electrodes 84a and 84b are formed, and are formed so that one surface of each of the first and second retaining plates 74a and 74b covers the region on which the second electrodes 84a and 84b are formed.

Moreover, the first and second retaining plates 74a and 74b are tapered to have a smaller thickness at one end near the second insert opening 75 than that at the other end, as shown in FIGS. 9 and 10. As shown in FIG. 10, the first and second retaining members 74a and 74b are pressed by the clamp member 76 to connect the first electrodes 82a and 82b on the first and second boards 61a and 61b received in the socket portion 73 with the second electrodes 84a and 84b on the first and second retaining plates 74a and 74b, and fix the first and second boards 61a and 61b.

The clamp member 76 comprises first and second press plates 76a and 76b, and a press plate joint portion 77, as shown in FIGS. 9 and 10. The clamp member 76 is formed in a U shape in which the first and second press plates 76a and 76b face each other, and the first and second press plates 76a and 76b are joined at one end by the press plate joint portion 77. The clamp member 76 is also provided with a pressure adjusting member 101, and first and second press guide grooves 94a and 94b.

As shown in FIGS. 9 and 10, the first and second press plates 76a and 76b are tapered to have a larger thickness at one end near the second insert opening 75 than that at the other end corresponding to the thickness of the space between the side wall of the socket portion 73 running along a surface of the first and second retaining plates 74a and 74b and the other surface of each of the first and second retaining plates 74a and 74b on which no second electrodes 84a and 84b are formed. Moreover, the first and second press plates 76a and 76b have a larger area than the other surfaces of the second electrode plates 83a and 83b on which no second electrodes 84a and 84b are formed, and are formed to cover the other surfaces of the second electrode plates 83a and 83b.

The clamp member 76 is formed as insertable/removable into/from the socket portion 73 through the second insert opening as shown in FIG. 10. By inserting the first and second press plates 76a and 76b through the second insert opening 75, they come into contact with the side wall of the socket portion 73 running along a surface of the first and second retaining plates 74a and 74b and the other surfaces of the first and second retaining plates 74a and 74b on which no second electrodes 84a and 84b are formed to press the first and second retaining plates 74a and 74b, whereby the clamp member 76 connects the first electrodes 82a and 82b with the second electrodes 84a and 84b. Moreover, the clamp member 76 is removed from the socket portion 73 by withdrawing the first and second press plates 76a and 76b through the second insert opening 75, whereby the pressure on the first and second retaining plates 74a and 74b is released, and the first electrodes 82a and 82b and second electrodes 84a and 84b are disconnected.

The pressure adjusting member 101 is provided in the clamp member 76 for adjusting the distance over which the clamp member 76 may be inserted from the second insert opening 75. The pressure adjusting member 101 comprises a head 102, and a threaded portion 103 joined to the head 102. A tapped hole portion 104 for fitting therein the threaded portion 103 is formed through the press plate joint portion 77 at one end of the clamp member 76. The pressure adjusting member 101 adjusts the distance over which the clamp member 76 may be inserted from the second insert opening 75 to adjust pressure by rotating the head 102 in a certain direction to move the threaded portion 103 through the tapped hole portion 104. The pressure adjusting member 101 adjusts the distance over which the clamp member 76 may be inserted from the second insert opening 75 to a shorter distance by moving the tip of the threaded portion 103 in a direction away from the press plate joint portion 77 at one end of the clamp member 76, and on the other hand, adjusts the distance over which the clamp member 76 may be inserted from the second insert opening 75 to a longer distance by moving the tip of the threaded portion 103 toward the press plate joint portion 77 at one end of the clamp member 76.

The first and second press guide grooves 94a and 94b are formed in the first and second press plates 76a and 76b corresponding to the first and second guide rods 91R and 91L for guiding the clamp member 76 inserted through second insert opening 75 in position. In the present embodiment, the first and second press guide grooves 94a and 94b are each constituted as a groove longer than the distance between the first and second guide rods 91R and 91L. By inserting the first and second press guide grooves 94a and 94b to fit over the first and second guide rods 91R and 91L, the first and second press plates 76a and 76b are received in the socket portion 73 in position.

Now an operation of connecting or disconnecting the first electrodes 82a and 82b formed in the first electrode plates 81a and 81b on the boards 61a and 61b with the second electrodes 84a and 84b formed in the second electrode plates 83a and 83b on the retaining plates 74a and 74b in the connector 50 of the present embodiment in accordance with the present invention will be described with reference to FIGS. 9 and 10.

When the first electrodes 82a and 82b and second electrodes 84a and 84b are to be connected, the first and second boards 61a and 61b provided on one surface each with the first electrodes 82a and 82b are first placed with the other surfaces of the first and second boards 61a and 61b abutted against each other. Then, as shown in FIG. 9, the first and second retaining plates 74a and 74b are moved in the inside of the socket portion 73 in the direction of axes of the first and second guide rods 91R and 91L, whereby a space for allowing insertion of the mutually abutting first and second boards 61a and 61b is created in the socket portion 73.

As shown in FIG. 10(a), the mutually abutting first and second boards 61a and 61b are inserted through the first insert opening 72 into the space between the first and second retaining plates 74a and 74b so that the first electrodes 82a and 82b face the corresponding second electrodes. Then, the board guide cuts 92R and 92L in the first and second boards 61a and 61b are inserted to fit over the first and second guide rods 91R and 91L.

As shown in FIG. 10(b), the first and second press plates 76a and 76b of the clamp member 76 are then inserted through the second insert opening 75 by a distance for insertion adjusted by the pressure adjusting member 101. By inserting the first and second press plates 76a and 76b through the second insert opening 75, the surfaces of the first and second press plates 76a and 76b come into contact with the side wall of the socket portion 73 running along a surface of the first and second retaining plates 74a and 74b and the other surfaces of the first and second retaining plates 74a and 74b on which no second electrodes 84a and 84b are formed to press the first and second retaining plates 74a and 74b, whereby the first electrodes 82a and 82b are connected with the second electrodes 84a and 84b. In the course of inserting the first and second press plates 76a and 76b of the clamp member 76 through the second insert opening 75, the first and second press guide grooves 94a and 94b are inserted to fit over the first and second guide rods 91R and 91L.

On the other hand, when the first electrodes 82a and 82b and second electrodes 84a and 84b are to be disconnected, the first and second press plates 76a and 76b are withdrawn through the second insert opening 75 to release pressure onto the first and second retaining plates 74a and 74b, whereby the first electrodes 82a and 82b and second electrodes 84a and 84b are disconnected. The mutually abutting first and second boards 61a and 61b are then withdrawn through the first insert opening 72.

Thus, according to the present embodiment, by inserting the clamp member 76 through the second insert opening 75 into the socket portion 73, the surfaces of the clamp member 76 come into contact with the surface of the retaining member 74 and the side wall of the socket portion 73 running along a surface of the retaining member 74 to press the retaining member 74, whereby the boards 61a and 61b received in the socket portion 73 are fixed to connect the first electrodes 82a and 82b with the second electrodes 84a and 84b. Since the retaining member 74 is tapered to have a smaller thickness at one end near the second insert opening 75 than that at the other end, and the clamp member 76 is tapered to have a larger thickness at one end near the second insert opening 75 than that at the other end, the clamp member 76 is easily inserted through the second insert opening 75 into the socket portion 73, and the other end of the socket portion 73 on the opposite side of the second insert opening 75 is easily pressed, whereby the board can be fixed with uniform rigidity and the first electrodes 82a and 82b can be connected with the second electrodes 84a and 84b. Moreover, even if a plurality of boards are disposed in a small space as in the aforementioned X-ray detector array 23, the boards 61a and 61b can be easily fixed by inserting the clamp member 76 through the second insert opening 75.

Furthermore, the retaining member 74 has one surface formed to cover a region in which the first electrodes 82a and 82*b* are connected with the second electrodes 84*a* and 84*b*. Thus, the retaining member 74 presses and fixes the boards 61*a* and 61*b* with uniform rigidity throughout the socket portion 73, and the first electrodes 82*a* and 82*b* and second electrodes 84*a* and 84*b* can be connected with uniform rigidity.

The clamp member 76 has one surface formed to cover the other surface of the retaining member 74 on which no second electrodes 84*a* and 84*b* are formed, and is formed to have a thickness corresponding to that of the space between the side wall of the socket portion 73 running along a surface of the retaining member 74 and the other surface of the retaining member 74. Thus, the clamp member 76 presses and fixes the boards 61*a* and 61*b* with uniform rigidity throughout the socket portion 73, and the first electrodes 82*a* and 82*b* and second electrodes 84*a* and 84*b* can be connected with uniform rigidity.

In addition, the clamp member 76 is formed to be insertable/removable through the second insert opening 75 into/from the socket portion 73. Thus, insertion/removal of the boards 61*a* and 61*b* in a small space is easy, thus facilitating maintenance work for a radiation tomographic imaging apparatus such as an X-ray CT apparatus.

The clamp member 76 is provided with the pressure adjusting member 101 for adjusting the distance over which the clamp member 76 may be inserted from the second insert opening 75. In the present embodiment, the pressure adjusting member 101 comprises the head 102 and the threaded portion 103 joined to the head 102, the tapped hole portion 104 for fitting therein the threaded portion 103 is formed at one end of the clamp member 76, and the distance over which the clamp member 76 may be inserted from the second insert opening 75 is adjusted by rotating the head 102 in a certain direction to move the threaded portion 103 through the tapped hole portion 104. Thus, the clamp member 76 presses and fixes the boards 61*a* and 61*b* with appropriate rigidity to connect the first electrodes 82*a* and 82*b* with the second electrodes 84*a* and 84*b* with appropriate rigidity, thereby facilitating insertion/removal. Moreover, in the present embodiment, since the pressure adjusting member 101 is comprised of the head 102 and threaded portion 103, it is easy to finely adjust the distance over which the clamp member 76 may be inserted from the second insert opening 75.

Moreover, the connector body 75 is provided with the guide member 91 for guiding the boards 61*a* and 61*b* inserted through the first insert opening 72 in position. In the present embodiment, the first and second guide rods 91R and 91L are provided as the guide member 91 at one end of the socket portion 73 near the second insert opening 75 and at the other end on the opposite side, with their ends fixed to the side walls of the socket portion running along a surface of the retaining member 74. Thus, the position into which the boards 61*a* and 61*b* are to be inserted and received can be easily ascertained, thereby facilitating insertion/removal. Furthermore, since the first and second guide rods 91R and 91L are provided at one end of the socket portion 73 near the second insert opening 75 and at the other end on the opposite side, the boards 61*a* and 61*b* can be supported even when they are not pressed, thereby facilitating insertion/removal.

Furthermore, the clamp member 76 is provided with the press guide grooves 94*a* and 94*b* corresponding to the first and second guide rods 91L and 91R to guide the clamp member 76 inserted through the second insert opening 75 in position using the first and second guide rods 91L and 91R. Thus, the position into which the clamp member 76 is inserted and received through the second insert opening 75 can be easily ascertained, thereby facilitating insertion/removal. In addition, since the first and second guide rods 91L and 91R are used for positioning of both the boards 61*a* and 61*b* and clamp member 76, the space within the socket portion 73 can be efficiently used.

Moreover, the retaining member 74 comprises the first through holes 93R*a* and 93R*b* through which the first guide rod 91R runs and the second through holes 93L*a* and 93L*b* through which the second guide rod 91L runs. Thus, the retaining member 74 can be easily disposed in position in the socket portion 73, thereby facilitating insertion/removal.

The retaining member 74 is provided to be movable in the socket portion 73 in the direction of axes of the first guide rod 91R running through the first through holes 93R*a* and 93R*b* and of the second guide rod 91L running through the second through holes 93L*a* and 93L*b*. Thus, a space for receiving the boards 61*a* and 61*b* is easily created in the socket portion 73, thereby facilitating insertion/removal.

Therefore, according to the present embodiment, even if the space for disposing a board is small, the board is easily fixed to the connector with sufficient rigidity, and the board is easily inserted/removed into/from the connector, thereby facilitating maintenance work.

It should be noted that the present invention is not limited to being practiced in the aforementioned embodiments, and various modifications can be employed.

For example, while a case in which two boards are received in the socket portion in the connector body in the aforementioned embodiments is described, the present invention is not limited thereto. For example, the present invention can be applied to a case in which one board is to be received.

Moreover, for example, while two retaining members and two clamp member are employed in the aforementioned embodiments, the present invention is not limited thereto. For example, one retaining member and one clamp member may be used to abut one surface of the board against the side wall of the socket portion, and press and fix the other surface of the board by the retaining member and clamp member.

Many widely different embodiments of the invention may be configured without departing from the spirit and the scope of the present invention. It should be understood that the present invention is not limited to the specific embodiments described in the specification, except as defined in the appended claims.

The invention claimed is:

1. A connector comprising:
    a connector body provided with a first insert opening for inserting therethrough a board, and a socket portion for receiving at least part of said board inserted through said first insert opening;
    a retaining member disposed in said socket portion with its one surface facing a surface of said board so that said retaining member is pressed to fix said board received in said socket portion; and
    a clamp member for pressing said retaining member by coming into contact with a side wall of said socket portion running along a surface of said retaining member and the other surface of said retaining member,
    wherein said connector body is provided with a second insert opening for inserting therethrough said clamp member, said second insert opening communicating with said socket portion,
    said retaining member is formed to have a smaller thickness at one end near said second insert opening than that at the other end, and said clamp member is formed to have a larger thickness at one end near said second insert opening than that at the other end, is inserted through said second insert opening into said socket portion to press said retaining member, and is formed to be insertable/removable through said second insert opening into/from said socket portion.

2. A connector comprising:

a connector body provided with a first insert opening for inserting therethrough a board, and a socket portion for receiving at least part of said board inserted through said first insert opening;

a retaining member disposed in said socket portion with its one surface facing a surface of said board so that said retaining member is pressed to fix said board received in said socket portion; and a clamp member for pressing said retaining member by coming into contact with a side wall of said socket portion running along a surface of said retaining member and the other surface of said retaining member, wherein said connector body is provided with a second insert opening for inserting therethrough said clamp member, said second insert opening communicating with said socket portion, said retaining member is formed to have a smaller thickness at one end near said second insert opening than that at the other end, and said clamp member is formed to have a larger thickness at one end near said second insert opening than that at the other end, is inserted through said second insert opening into said socket portion to press said retaining member, and is provided with a pressure adjusting member for adjusting a distance over which said clamp member may be inserted from said second insert opening.

3. The connector of claim 2, wherein:

said pressure adjusting member comprises a head and a threaded portion joined to said head, a tapped hole portion for fitting therein said threaded portion is formed in said clamp member at one end, and the distance over which said clamp member may be inserted from said second insert opening is adjusted by rotating said head in a certain direction to move said threaded portion through said tapped hole portion.

4. A connector comprising:

a connector body provided with a first insert opening for inserting therethrough a board, and a socket portion for receiving at least part of said board inserted through said first insert opening, wherein said connector body is provided with a guide member for guiding said board inserted through said first insert opening in position;

a retaining member disposed in said socket portion with its one surface facing a surface of said board so that said retaining member is pressed to fix said board received in said socket portion; and a clamp member for pressing said retaining member by coming into contact with a side wall of said socket portion running along a surface of said retaining member and the other surface of said retaining member, wherein said connector body is provided with a second insert opening for inserting therethrough said clamp member, said second insert opening communicating with said socket portion, said retaining member is formed to have a smaller thickness at one end near said second insert opening than that at the other end, and said clamp member is formed to have a larger thickness at one end near said second insert opening than that at the other end, is inserted through said second insert opening into said socket portion to press said retaining member.

5. The connector of claim 4, wherein:

said retaining member has a through hole through which said guide rod runs.

6. The connector of claim 5, wherein:

said retaining member is provided to be movable in said socket portion in a direction of an axis of said guide rod running through said through hole.

7. The connector of claim 4, wherein:

said guide member is a guide rod formed to be fixed at its ends to the side wall of said socket portion running along a surface of said retaining member.

8. The connector of claim 7, wherein:

said clamp member is formed with a press guide groove corresponding to said guide rod for guiding said clamp member inserted through said second insert opening in position using said guide rod.

9. The connector of claim 7, comprising:

as said guide rod, a first guide rod formed at one end of said socket portion near said second insert opening and a second guide rod formed at the other end of said socket portion on the opposite side of said second insert opening.

10. The connector of claim 9, wherein:

said clamp member is provided with press guide grooves corresponding to said first and second guide rods for guiding said clamp member inserted through said second insert opening in position using said first and second guide rods.

11. The connector of claim 9, wherein:

said retaining member has a first through hole through which said first guide rod runs and a second through hole through which said second guide rod runs.

12. The connector of claim 11, wherein:

said retaining member is provided to be movable in said socket portion in a direction of axes of said first guide rod running through said first through hole and of said second guide rod running through said second through hole.

13. A radiation tomographic imaging apparatus comprising: a detecting device in which detector elements are disposed for detecting radiation emitted to an imaged region in a subject to be imaged and passing through said imaged region, and for outputting projection data; a collecting device comprising a board provided on at least one surface with first electrodes to which said projection data from said detector elements is input, and formed with a driving circuit for collecting said input projection data; and a connector provided with, corresponding to said first electrodes, second electrodes for outputting the projection data from said detector elements to said first electrodes, for connecting said first electrodes with said second electrodes, said connector comprising:

a connector body provided with a first insert opening for inserting therethrough said board, and a socket portion for receiving said first electrodes on said board inserted through said first insert opening;

a retaining member provided on one surface with said second electrodes facing said first electrodes when said board is inserted, and disposed in said socket portion so that said retaining member is pressed to connect said first electrodes with said second electrodes and fix said board received in said socket portion; and a clamp member for pressing said retaining member by coming into contact with a side wall of said socket portion running along a surface of said retaining member and the other surface of said retaining member, wherein said connector body is provided with a second insert opening for inserting therethrough said clamp member, said second insert opening communicating with said socket portion, said retaining member is formed to have a smaller thickness at one end near said second insert opening than that at the other end, and said clamp member is formed to have a larger thickness at one end near said second insert opening than that at the other end, and is inserted through said second insert opening into said socket portion to press said retaining member.

14. The radiation tomographic imaging apparatus of claim 13, wherein:

one surface of said retaining member is formed to cover a region in which said first electrodes are connected with said second electrodes.

15. The radiation tomographic imaging apparatus of claim 13, wherein:

one surface of said clamp member is formed to cover the other surface of said retaining member.

* * * * *